US009956315B2

(12) United States Patent
Patel et al.

(10) Patent No.: US 9,956,315 B2
(45) Date of Patent: May 1, 2018

(54) FISTULA GRAFT WITH DEFORMABLE SHEET-FORM MATERIAL

(75) Inventors: Umesh H. Patel, West Lafayette, IN (US); F. Joseph Obermiller, West Lafayette, IN (US); Clay D. Fette, Palm Beach Gardens, FL (US); Matthew R. Graham, Fort Wayne, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 2152 days.

(21) Appl. No.: 11/414,682

(22) Filed: Apr. 28, 2006
(Under 37 CFR 1.47)

(65) Prior Publication Data
US 2007/0088445 A1 Apr. 19, 2007

Related U.S. Application Data

(60) Provisional application No. 60/676,482, filed on Apr. 29, 2005.

(51) Int. Cl.
*A61F 2/06* (2013.01)
*A61L 27/36* (2006.01)
(Continued)

(52) U.S. Cl.
CPC ...... *A61L 27/3604* (2013.01); *A61B 17/0057* (2013.01); *A61K 35/22* (2013.01);
(Continued)

(58) Field of Classification Search
CPC ....... A61F 2/04; A61B 17/12; A61B 17/0057; A61B 2017/00641
(Continued)

(56) References Cited

U.S. PATENT DOCUMENTS 2,127,903 A 8/1938 Bowen
4,511,653 A 4/1985 Play et al.
(Continued)

FOREIGN PATENT DOCUMENTS

RU 2180529 C2 3/2002
SU 1673130 A1 8/1991
(Continued)

OTHER PUBLICATIONS

Heeschen, C., et al. "Nicotine Stimulates Angiogenesis and Promotes Tumor Growth and Atherosclerosis". Nature Medicine, vol. 7., No. 7, Jul. 2001. pp. 833-839.
(Continued)

*Primary Examiner* — Gregory Anderson
*Assistant Examiner* — Christina Lauer
(74) *Attorney, Agent, or Firm* — Woodard, Emhardt, Moriarty, McNett & Henry LLP

(57) ABSTRACT

Described are medical products, systems, and methods for treating fistulae having a primary opening, such as in the alimentary canal. Certain methods of the invention include providing an implantable material including a compliant sheet form biocompatible material, and forcing this sheet form biocompatible material into the primary opening so as to deform the sheet form biocompatible material to conform to and block the primary opening. The biocompatible material preferably comprises a remodelable material, for example, a remodelable extracellular matrix material such as submucosa.

27 Claims, 3 Drawing Sheets

(51) Int. Cl.
*A61B 17/00* (2006.01)
*A61K 35/22* (2015.01)
*A61K 35/38* (2015.01)
*A61L 31/00* (2006.01)

(52) U.S. Cl.
CPC ............ *A61K 35/38* (2013.01); *A61L 31/005* (2013.01); *A61B 2017/00641* (2013.01)

(58) Field of Classification Search
USPC ...................................... 606/213; 600/23.72
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 4,981,465 A | 1/1991 | Ballan | |
| 5,192,302 A * | 3/1993 | Kensey et al. | 606/213 |
| 5,275,826 A | 1/1994 | Badylak et al. | |
| 5,281,422 A | 1/1994 | Badylak et al. | |
| 5,334,216 A | 8/1994 | Vidal | |
| 5,356,432 A * | 10/1994 | Rutkow et al. | 623/23.72 |
| 5,374,261 A | 12/1994 | Yoon | |
| 5,397,331 A * | 3/1995 | Himpens et al. | 606/151 |
| 5,516,533 A | 5/1996 | Badylak et al. | |
| 5,554,389 A | 9/1996 | Badylak et al. | |
| 5,584,827 A | 12/1996 | Korteweg | |
| 5,628,762 A | 5/1997 | Moshin | |
| 5,643,305 A | 7/1997 | Moshin | |
| 5,752,974 A | 5/1998 | Rhee | |
| 5,755,791 A | 5/1998 | Whitson et al. | |
| 5,955,110 A | 9/1999 | Patel et al. | |
| 5,993,844 A | 11/1999 | Abraham et al. | |
| 5,997,575 A | 12/1999 | Whitson et al. | |
| 6,090,996 A | 7/2000 | Li | |
| 6,099,567 A | 8/2000 | Badylak et al. | |
| 6,206,931 B1 | 3/2001 | Cook et al. | |
| 6,375,989 B1 | 4/2002 | Badylak et al. | |
| 6,569,081 B1 | 5/2003 | Nielsen | |
| 6,666,892 B2 | 12/2003 | Hiles et al. | |
| 2001/0027347 A1 * | 10/2001 | Rousseau | 623/23.72 |
| 2002/0188317 A1 * | 12/2002 | Rousseau | 606/213 |
| 2003/0013989 A1 | 1/2003 | Obermiller et al. | |
| 2003/0032961 A1 * | 2/2003 | Pelo et al. | 606/72 |
| 2003/0051735 A1 | 3/2003 | Pavcnik et al. | |
| 2003/0125766 A1 * | 7/2003 | Ding | 606/213 |
| 2004/0158185 A1 | 8/2004 | Moran et al. | |
| 2004/0215231 A1 * | 10/2004 | Fortune et al. | 606/213 |
| 2005/0013844 A1 | 1/2005 | Hadlock et al. | |
| 2005/0049626 A1 * | 3/2005 | Burgard | 606/191 |
| 2005/0070759 A1 * | 3/2005 | Armstrong | 600/105 |
| 2005/0155608 A1 | 7/2005 | Pavcnik et al. | |
| 2005/0159776 A1 | 7/2005 | Armstrong | |
| 2005/0182495 A1 | 8/2005 | Perrone | |
| 2007/0031508 A1 | 2/2007 | Armstrong et al. | |

FOREIGN PATENT DOCUMENTS

| | | |
|---|---|---|
| SU | 1690737 A1 | 11/1991 |
| SU | 1718837 | 3/1992 |
| WO | WO 96/31226 A | 10/1996 |
| WO | WO 98/22158 | 5/1998 |
| WO | WO 98/25637 | 6/1998 |
| WO | WO 00/74576 * | 7/1999 |
| WO | WO 00/09024 | 2/2000 |
| WO | WO 2000/72759 A2 | 12/2000 |
| WO | WO 03/009764 | 2/2003 |
| WO | WO 05/020847 | 3/2005 |
| WO | WO 2005/020823 A1 | 3/2005 |
| WO | WO 2006/119256 A2 | 11/2006 |
| WO | WO 2007/002260 A2 | 1/2007 |
| WO | WO 2007/064819 A2 | 6/2007 |
| WO | WO 2007/090150 A2 | 8/2007 |
| WO | WO 2007/090155 A1 | 8/2007 |

OTHER PUBLICATIONS

Johnson, C., et al. "Matrix Metalloproteinase-9 is Required for Adequate Angiogenic Revascularization of Ischemic Tissues: Potential Role in Capillary Branching". Circulation Research, vol. 94. (2004) pp. 262-268.

Maluf-Filho, F. et al. "Endoscopic Treatment of Esophagogastric Fistulae with an Acellular Matrix". Gastrointestinal Endoscopy, Elsevier, NL, vol. 59, No. 5, Apr. 2004 (Apr. 2004), p. 151, XP004854594 abstract.

Schultz, D. J. et al. "Porcine small intestine submucosa as a treatment for enterocutaneous fistulas". Journal of the American College of Surgeons, College, Chicago, IL, vol. 194, No. 4, Apr. 2002 (Apr. 2002), pp. 541-543, XP003004342.

Himpson, Rebecca C., et al. "Histological evidence for enhanced anal fistula repair using autologous fibroblasts in a dermal collagen matrix". Comparative Clinical Pathology, Apr. 2006, vol. 16, No. 1.

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Moore, Robert D., et al. "Rectovaginal Fistula Repair Using a Porcine Dermal Graft". Obstetrics & Gynecology, 2004, 104, 1165-1167.

Schwesinger, Wayne H., "Management of Persistent Fistula After Gastrectomy" on-line question (www.medscape.com), posted on May 14, 2002.

Shah, A. M., et al. "Bronchoscopic closure of bronchopleural fistula using gelfoam" abstract. Journal of Association of Physicians of India, 2004, vol. 52, No. JUIN, pp. 508-509.

Shaker MA, Hindy AM, Mounir RM, Geaisa KM. Egypt Dent J. Jul. 1995; 41(3): 1237-42.

Sheiman, Robert G., et al. "Percutaneous Treatment of a Pancreatic Fistula after Pancreaticoduodenectomy". J Vasc Interv Radiol, 2001, vol. 12, No. 4, pp. 524-526.

Shelton, Andrew A., et al. Transperineal Repair of Persistent Rectovaginal Fistulas Using an Acellular Cadaveric Dermal Grant (AlloDerm®). Diseases of the Colon & Rectum, Sep. 2006, vol. 49, No. 9.

U.S. Appl. No. 11/766,606, filed Jun. 6, 2007 to Obermiller et al.

Wilson Gunn on behalf of unnamed party, Letter to The European Patent Office, Jan. 30, 2007, pp. 1-4.

Schultz D J et al: "Porcine small intestine submucosa as a treatment for enterocutaneous fistulae" Journal of the American College of Surgeons, College, Chicago, IL, US, vol. 194, No. 4, Apr. 2002, pp. 541-543.

* cited by examiner

FISTULA GRAFT WITH DEFORMABLE SHEET-FORM MATERIAL

This application claims the benefit of priority of U.S. Provisional Patent Application Ser. No. 60/676,482 filed Apr. 29, 2005 which is incorporated herein by reference in its entirety.

BACKGROUND

The present invention relates generally to medical devices and in particular aspects to medical products and methods for treating fistulae having a primary opening in the alimentary canal.

As further background, a variety of fistulae can occur in humans. These fistulae can occur for a variety of reasons, such as but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

The path which these fistulae take, and their complexity, can vary. A fistula may take a take a "straight line" path from the primary to the secondary opening, known as a simple fistula. Alternatively, the fistula may consist of multiple tracts ramifying from the primary opening and have multiple secondary openings. This is known as a complex fistula.

The anatomic path which a fistula takes is classified according to its relationship to the anal sphincter muscles. The anal sphincter consists of two concentric bands of muscle, the inner or internal sphincter and the outer or external anal sphincter. Fistulae which pass between the two concentric anal sphincters are known as inter-sphincteric fistulae. Those which pass through both internal and external sphincters are known as trans-sphincteric fistulae, and those which pass above both sphincters are called supra-sphincteric fistula. Fistulae resulting from Crohn's disease usually "ignore" these anatomic planes, and are known a "extra-anatomic" fistulae.

Many complex fistulae consist of multiple tracts, some blind-ending and others leading to multiple secondary openings. One of the most common complex fistulae is known as a horseshoe fistula. In this instance, the infection starts in the anal gland (primary opening) at or near the 12 o'clock location (with the patient in the prone position). From this primary opening, fistulae pass bilaterally around the anal canal, in a circumferential manner. Multiple secondary openings from a horseshoe fistula may occur anywhere around the periphery of the anal canal, resulting in a fistula tract with a characteristic horseshoe configuration.

One technique for treating a perianal fistulae is to make an incision adjacent the anus until the incision contacts the fistula and then excise the fistula from the anal tissue. This surgical procedure tends to sever the fibers of the anal sphincter, and may cause incontinence.

Other surgical treatment of fistulae involve passing a fistula probe through the tract of the fistula in a blind manner, using primarily only tactile sensation and experience to guide to probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

Still other methods involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and allows the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative medical products, methods, and systems that are useful for treating fistulae. The present invention is addressed to those needs.

SUMMARY

The present invention provides, in certain aspects, unique methods for treating fistulae having a primary opening, such as in the alimentary canal. Certain embodiments of the invention relate to methods for treating anorectal fistulae that involve blocking the primary opening of the fistula with an implant material shaped differently than the opening but being sufficiently deformable to shape to and fill the opening. For example, some inventive methods include providing an implantable material including a deformable sheet form biocompatible material, and forcing this sheet form biocompatible material into the primary opening so as to deform the sheet form biocompatible material to conform to and block the opening. Such forcing can be accomplished in any suitable manner including but not limited to pushing or pulling the sheet form biocompatible material into the primary opening. The biocompatible material preferably comprises a remodelable material, for example, a remodelable extracellular matrix material such as submucosa. Also, the sheet form biocompatible material can be provided in a single layer or multilayer form.

In one particular embodiment, the invention provides a medical product for treating a fistula having a primary opening in the alimentary canal. This medical product comprises an implantable material including a compliant sheet form biocompatible material. The sheet form biocompatible material is deformable upon impingement by soft tissue surrounding the primary opening of the fistula, and is sized and shaped so as to be deformable to a three-dimensional volumetric body filling the primary opening of the fistula. Such a three-dimensional volumetric body, when formed, can include a portion extending into the fistula tract, and potentially protruding through a secondary opening of the fistula. In certain aspects, the implantable material includes a conical tip with one or more sheets extending therefrom. These sheets may or may not be planar, and in some forms, include a plurality of folds, e.g., are fan-folded.

Another embodiment of the present invention provides a method for treating a fistula having a primary opening in the alimentary canal, the fistula defining a void through soft tissues, wherein the void includes a fistula tract and a primary opening. This method includes providing an implantable material including a deformable sheet form biocompatible material. Further, this method includes forcing the sheet form biocompatible material into the void so as to deform the sheet form biocompatible material into a three-dimensional volumetric body impinging upon soft tissue surfaces of the void and blocking at least a segment of the void. In certain aspects, this method can include, as examples, blocking the void at the primary opening, blocking the fistula tract (or any segment thereof), or both.

Yet another embodiment of the invention provides a medical product for treating a fistula having a primary opening in the alimentary canal, the fistula defining a void through soft tissues, wherein the void includes a fistula tract and a primary opening. Such a medical product comprises an implantable material including a compliant sheet form biocompatible material. This sheet form biocompatible material is deformable upon forcible contact against soft tissue surfaces defining the void. Further, this sheet form biocompatible material is sized and shaped so as to be deformable to a three-dimensional volumetric body impinging upon the soft tissue surfaces and blocking at least a segment of the void. The implantable material can include any suitable biocompatible material, for example, a collagenous material and particularly a remodelable collagenous material. In certain aspects, the medical product includes an adaptation, which may or may not be integral with the product, to aid or facilitate deployment of the product within a patient. As just one example, such an adaptation may comprise an absorbable suture in association with the product. In some forms, this suture can be used to draw the product into the void defined by the fistula and/or secure the product to soft tissues surrounding the fistula. In certain aspects, the implantable material includes a leading portion, e.g., a generally conical head, and at least one sheet form trailing portion.

A further embodiment of the invention provides a medical kit. This medical kit includes a medical product such as those described above enclosed within a sealed package. In certain aspects, the medical kit includes a deployment device for forcing the medical product into the primary opening of a fistula. Further, the sealed package can include indicia identifying the contents of the package for use in treating a fistula.

In another embodiment, the invention provides a medical product for treating an opening within the body of a patient. This medical product comprises an implantable material including a leading portion and at least one trailing portion extending from the leading portion. The leading portion comprises a tapered three-dimensional body having a leading tip of a relatively smaller cross-sectional dimension which tapers to a segment of a relatively larger cross-sectional dimension. The at least one trailing portion includes a compliant sheet form biocompatible material. The sheet form biocompatible material is deformable upon impingement by tissue surrounding the opening, and is sized and shaped so as to be deformable to a trailing three-dimensional volumetric body filling the opening.

In still another embodiment, the invention provides a method of treating a void extending through tissue of a patient, the void having a first opening, a second opening, and a tract therethrough. This method comprises: (i) providing an implantable material including a deformable sheet form biocompatible material; and (ii) forcing this implantable material through the void to extend from the first opening through the tract and out of the second opening, wherein such forcing causes the sheet form biocompatible material to deform to a three dimensional volumetric body filling the first opening. In certain aspects, the sheet form biocompatible material includes at least one tapered portion.

Other embodiments, forms, features, advantages, aspects, and benefits of the present invention shall become apparent from the detailed description and drawings included herein.

DETAILED DESCRIPTION

Figure 1:
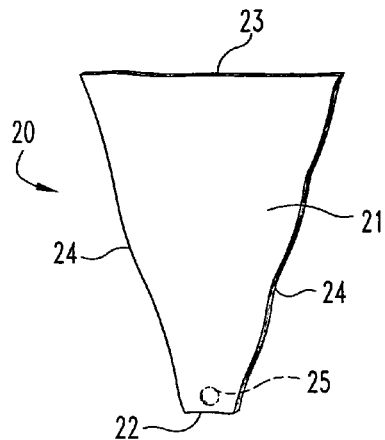
FIG. 1 is a perspective view of a medical product of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique medical products and methods for treating fistulae. For example, certain inventive methods include providing an implantable material including a deformable sheet form biocompatible material, and forcing this sheet form biocompatible material into the primary opening of an anorectal fistula so as to deform the sheet form biocompatible material to conform to and block the primary opening. The biocompatible material preferably comprises a remodelable material, for example, a remodelable extracellular matrix material such as submucosa. The invention also provides medical kits that include such medical products enclosed within sterile packaging.

The materials used to form the medical products of the present invention should generally be biocompatible, and in advantageous embodiments of the products, use a remodelable material. Particular advantage can be provided by medical products including a remodelable collagenous material. Such remodelable collagenous materials can be provided, for example, by collagenous materials isolated from a warm-blooded vertebrate, and especially a mammal. Such isolated collagenous material can be processed so as to have remodelable properties and promote cellular invasion and ingrowth. Remodelable materials may be used in this context to promote cellular growth on, around, or within tissue in which a medical product of the invention is implanted, e.g., on, around, or within a fistula tract or opening to a fistula.

Suitable bioremodelable materials can be provided by collagenous extracellular matrix (ECM) materials, possessing biotropic properties, including in certain forms angiogenic collagenous extracellular matrix materials. For example, suitable collagenous materials include ECM materials such as submucosa, renal capsule membrane, dermal collagen (including processed dermal collagen from human cadavers which can be used as allografts in human patients), dura mater, pericardium, facia lata, serosa, peritoneum or basement membrane layers, including liver basement membrane. Any of these ECM materials or other suitable materials can be used in uninterrupted sheet form, or may be physically modified such as, for example, by perforations or slits, including meshed patterns formed by a plurality of slits in the materials. Such physical modifications may be sufficiently incorporated to increase the conformability of the material, and/or for other purposes. Suitable submucosa materials for these purposes include, for instance, intestinal submucosa, including small intestinal submucosa, stomach submucosa, urinary bladder submucosa, and uterine submucosa. The preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94(2004), No. 2, 262-268.

Submucosa or other ECM tissue used in embodiments of the invention can be preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. Further, the submucosa and other ECM tissue materials of the present invention can be employed as xenografts (i.e., cross species, such as a non-human donor for a human recipient), allografts (i.e., intraspecies with a donor of the same species as the recipient) and/or autografts (i.e., the donor and the recipient being the same individual).

As prepared and used, the submucosa material or any other ECM material may optionally retain and/or include growth factors or other bioactive components native to the source tissue. For example, a submucosa or other remodelable ECM tissue material may include or retain one or more growth factors such as but not limited to basic fibroblast growth factor (FGF-2), transforming growth factor beta (TGF-beta), epidermal growth factor (EGF), and/or platelet derived growth factor (PDGF). As well, submucosa or other ECM materials when used in the invention may include other native bioactive agents such as but not limited to proteins, glycoproteins, proteoglycans, and glycosaminoglycans. Additionally, ECM material may include other biological materials such as heparin, heparin sulfate, hyaluronic acid, fibronectin, cytokines, and the like. Thus, generally speaking, a submucosa or other ECM material may include one or more bioactive components that induce, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods (e.g., genetic material such as DNA), may be incorporated into an ECM material of the invention. These non-native bioactive components may be naturally-derived or recombinantly produced proteins that correspond to those natively occurring in an ECM tissue, but perhaps of a different species (e.g., human proteins applied to collagenous ECMs from other animals, such as pigs). These non-native bioactive components may also be drug substances. Illustrative drug substances that may be added to (or incorporated within) the ECM material, such as one or more ECM layers, include, for example, anti-clotting agents, e.g. heparin, antibiotics, anti-inflammatory agents, thrombus-promoting substances such as blood clotting factors, e.g. thrombin, fibrinogen, and the like, and anti-proliferative agents, e.g. taxol derivatives such as paclitaxel. Such non-native bioactive components can be incorporated into and/or onto material of the invention in any suitable manner, for example, by surface treatment (e.g., spraying) and/or impregnation (e.g., soaking), just to name a few. Additionally, such agents can be applied to the ECM material as a pre-manufactured step, immediately prior to the procedure, or during or after engraftment of the ECM material within the patent.

ECM materials used in the invention may be free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In certain aspects, the invention provides medical products including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions.

An adhesive, glue or other bonding agent may also be used in achieving a bond between material layers of the invention. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents, such as glutaraldehyde, formaldehyde, epoxides, genipin or derivatives thereof, carbodiimide compounds, polyepoxide compounds, or other similar agents, including those others identified in the discussions above. Cross-linking of ECM materials can also be catalyzed by exposing the matrix to UV radiation, by treating the collagen-based matrix with enzymes such as transglutaminase and lysyl oxidase, and by photocross-linking. A combination of one or more of these with dehydration-induced bonding may also be used to bond ECM material layers to one another.

A variety of dehydration-induced bonding methods can be used to fuse together portions of an ECM material of the invention. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization, e.g., subjecting the materials to freeze-drying or evaporative cooling conditions. Lyophilization is also useful in drying operations involving medical products of the present invention. For example, a medical product including ECM material may be subjected to lyophilization conditions before placing it in packaging for transport or storage.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Medical products of the invention may include biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Suitable biocompatible implant materials of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Turning now to a discussion of particular medical products, systems, and methods of the present invention for treating fistulae having a primary opening in the alimentary canal, it should again be noted that a fistula can be described as defining a void through soft tissues, the void including a fistula tract, a primary opening, and potentially one or more secondary openings. Such fistulae can be treated in accordance with the present invention by blocking this void, or any portion thereof. For example, a method of the invention can include blocking the void at the primary opening, blocking the fistula tract (or a segment thereof), blocking any secondary openings, or any combination thereof.

Illustratively, a preferred fistula treatment method of the invention includes providing an implantable material including a compliant sheet form biocompatible material, and forcing this sheet form biocompatible material into the primary opening so as to deform the sheet form biocompatible material to conform to and block the primary opening. This sheet form biocompatible material is preferably deformable upon impingement by soft tissue surrounding the primary opening of the fistula. Such deformable materials can include any of the ECM and other biocompatible materials described herein. Further, this sheet form biocompatible material is preferably sized and shaped so as to be deformable to a three-dimensional volumetric body filling the primary opening of the fistula. In so doing, advantageous implant materials will also be sufficiently flaccid to avoid substantial cutting or tearing of the surrounding soft tissues.

In certain aspects, such a three-dimensional volumetric body, when formed, includes a portion extending into the fistula tract, and potentially into or protruding through any secondary openings of the fistula. This extending portion may or may not conform to and block other portions of the fistula void, i.e., those other than the primary opening, such as the fistula tract. Also, this extending portion can be used, in certain aspects, to attach the medical product to soft tissues at or near a secondary opening of the fistula as a means of preventing the product from reverse migrating undesirably back toward the alimentary canal. In desirable modes of operation, should amounts of the biocompatible implant material be protruding from the secondary opening, those amounts will be trimmed off such that the implant material no longer protrudes, and the newly-formed end can be sutured or otherwise secured in place under the skin if desired.

The medical products of the present invention, or any components thereof, can have any practical size and shape to treat a fistula having a primary opening in the alimentary tract of a vertebrate, especially a human. In general, the size and shape of the sheet form biocompatible material selected for a particular treatment application will be based, at least in part, on the general size and shape of the fistula being treated. In certain forms, the surgeon or other medical personnel can modify the provided product prior to deployment to suit a particular fistula treatment application, for example, by modifying the size and shape of the sheet form biocompatible material.

A sheet form biocompatible material of the invention is preferably sized and shaped such that the three-dimensional volumetric body, when formed, has a length of about 1 cm to about 50 cm, more typically from about 1 cm to about 15 cm, and even more typically from about 2 cm to about 10 cm. Likewise, it is preferable that the material's size and shape is such that at least a portion of the three-dimensional volumetric body, when formed, conforms to soft tissue surrounding the fistula to block at least the primary opening. Accordingly, any dimension of the sheet form biocompatible material (e.g., the material's thickness or the length of a side of the material, just to give a few examples) or any other property of the material (e.g., its density) can be varied so long as the three-dimensional volumetric body, when formed, is capable of blocking at least some segment of the fistula void.

In certain aspects, the sheet form biocompatible material is sized and shaped such that the three-dimensional volumetric body, when formed, conforms to and blocks the primary opening of a fistula. Preferably, such a three-dimensional volumetric body is capable of conforming to and blocking a primary opening having a diameter from about 1 to about 20 millimeters, more typically from about 5 to about 10 millimeters. In certain preferred aspects, such a three-dimensional volumetric body includes a remodelable material, for example, a remodelable ECM material. The bioactive nature of such materials promotes desirable healing of the fistula, for example, by overcoming the effects of bacteria and other deleterious substances typical to the fistula environment. In some forms, medical products of the invention incorporate an effective amount of an antimicrobial agent. Illustrative such agents include, for example, silver compounds such as silver salts (e.g. silver sulfate), dextran, chitosan, chlorhexidine, and nitric oxide donor compounds. Such agents can be incorporated throughout the medical product and/or on surfaces or selected regions thereof.

With reference now to FIG. 1, shown is a perspective view of an illustrative medical product 20 of the present invention. The product 20 comprises a compliant sheet form multilaminate material 21 including two layers of biocompatible material, e.g., small intestinal submucosa (SIS) bonded together. The sheet form material 21 has a first end 22, a second end 23 (opposite the first end 22), and diverging sides 24. (In other forms, the invention provides similar products that include a sheet form biocompatible material exhibiting other suitable geometrical shapes, for example, an isosceles triangle or any other suitable triangular or triangular-like shape, just to name a few.)

The sheet form SIS material 21 is preferably deformable upon impingement by soft tissues surrounding a fistula void, e.g., the primary opening and/or the fistula tract. Further, the sheet form SIS material 21 is preferably sized and shaped so as to be deformable to a three-dimensional volumetric body filling this void, or a segment thereof. Accordingly, to suit a particular fistula treatment application, the thickness of the material 21, as well as the lengths of the first end 22, second end 23, and diverging sides 24 can vary, and may depend on a number of factors including but not limited to one or more other properties or physical characteristics of the SIS material 21 (e.g., its degree of deformability) and/or the general size and shape of the fistula for which the product is designed to treat.

One way to alter the thickness of the sheet form SIS material 21, for example, is to compress it under dehydrating conditions, e.g., to vacuum press it. Another way to alter the thickness of the multilaminate sheet form SIS material is to alter the number of material layers included therein. Again, the sheet form SIS material 21 depicted in FIG. 1 includes two layers of remodelable SIS material bonded together. However, it should be noted that the sheet form SIS material 21 could be formed with any practical number of layers of material, including one, three, four, five, six, seven, eight, nine, ten, or more layers of SIS material. Also, any material layer included in a multilaminate sheet form material of the invention can have bonded and unbonded portions. For example, material layers may be bonded to one another proximate the first end 22 of the sheet form material 21 and not bonded to one another proximate the second end 23 of the sheet form material 21.

Continuing with FIG. 1, the medical product 20 is useful to treat fistulae in accordance with the present invention. Illustratively, the sheet form multilaminate SIS material 21 can be forced into an anorectal fistula void so as to deform the sheet form SIS material 21 to conform to and block the void, or any portion thereof. In certain aspects, occlusion is achieved with the entire deformed SIS sheet positioned within the void. In other aspects, occlusion of the void is achieved, wherein only a portion of the deformed SIS sheet is positioned therein.

The sheet form SIS material 21 can be forced into the fistula void in any suitable manner. For example, the sheet form SIS material 21 can be pushed or pulled into the void. In an illustrative embodiment, the first end 22 of the sheet form SIS material 21 is pulled into the fistula through the primary opening, and toward a secondary opening. This can be accomplished in any suitable manner. Illustratively, a pair of surgical hemostats, or a fistula probe, can be passed through a secondary opening and potentially out through the primary opening. The first end 22 of the SIS material 21 can then be grasped by the hemostats, or secured to the probe, and the material drawn into fistula tract through the primary opening. In certain illustrative embodiments, tissue surrounding the fistula tract is conditioned such that it initiates a healing response before the sheet form SIS material 21 is forced into the void.

In certain aspects, the sheet form SIS material 21 will be shaped and sized such that the diameter of the primary opening is greater than the width of the first end 22 but less than the width of the second end 23 of the material; however, in alternative embodiments, the sheet form material will be shaped and sized such that the volume occupied by the gathered sheet form material of the first end 22 is less than the volume occupied by the gathered sheet form material of the second end 23 when each of the ends are present within the primary opening of the fistula tract. In these aspects, as the SIS sheet form material 21 is drawn into the void, it folds and/or rolls over itself one or more times to conform to the primary opening, and is gradually "wedged" into the primary opening when sufficiently pulled through. Such wedging can for example be evidenced by an increasing resistance to passage of the sheet 21 as it is pushed or pulled into the primary opening. As the second end 23 becomes wedged into the primary opening, the deformed SIS material becomes lodged in place to block the void. Such wedging or lodging may be sufficient to obviate the need for otherwise securing the product to the soft tissues surrounding the fistula. Nonetheless, in certain aspects, the first end 22 and/or second end 23 is further secured to the soft tissues, for example, by suturing. Also, the first end 22 and/or second end 23 can be trimmed, for example, to prevent the engrafted SIS material from protruding undesirably from the primary opening and/or the secondary opening. In certain forms, deployment of a medical product of the invention is aided or facilitated by tracking the product along an emplaced guidewire.

In other embodiments, forcing the sheet form SIS material 21 into the fistula void involves pushing the sheet form material 21 into the void, or any portion thereof. Illustratively, the sheet form SIS material 21 can be inserted into the void with a suitable deployment device. For example, the medical product can be preloaded into a deployment device having an outer sheath. This deployment device can then be inserted into the void, for example, through a secondary opening so as to deform the sheet form SIS material 21 to conform to and fill at least the primary opening of the void. Thereafter, the sheath can be removed, leaving the deformed sheet from material deployed within the void, or any segment thereof.

In certain aspects, the three-dimensional volumetric body (i.e., the deformed sheet form biocompatible material) comprises a material receptive to tissue ingrowth. In such aspects, upon deployment of the medical product in accordance with the present invention, cells from the patient can infiltrate the material, leading to, for example, new tissue growth on, around, and/or within the three-dimensional volumetric body. In certain forms, such new tissue can also grow within any creases or crevices which were formed in and/or between the material as it folded and/or rolled over itself to conform to soft tissues surrounding the fistula void during product deployment. In some embodiments, a medical product deployed in accordance with the present invention comprises a remodelable material. In these embodiments, the remodelable material promotes the formation of new tissue, and is capable of being broken down and replaced by new tissue in such a way that the original fistula closure achieved by the three-dimensional volumetric body is maintained throughout the remodeling process so as to eventually form a closure or substantial closure with the new tissue.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical product of the invention (including any layer of ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure. In certain aspects, a sheet form biocompatible material of the invention is configured such that the three-dimensional volumetric body, when formed, has differential porosity along its length. For example, such a three-dimensional volumetric body may have a portion with a relatively more closed matrix structure blocking the primary opening of a fistula, and a portion with a relatively more open matrix structure extending into the fistula tract. Having material with a relatively more closed matrix structure at or near the primary opening can inhibit bacteria and other undesirable substances from passing into the alimentary canal from the fistula.

In certain aspects, the medical product 20 includes an adaptation (which may or may not be integral with the sheet form biocompatible material 21) for aiding or facilitating deployment of the product within a patient (or otherwise providing additional benefits to the patient as described below). As one example, such an adaptation may comprise an absorbable suture or other similar device in association with the product. An associated suture can be used to draw the product into the void defined by the fistula and/or secure the product to soft tissues surrounding the fistula following product placement. Additionally, such an adaptation can incorporate one or more barbs or other suitable devices that are useful for de-epithelializing or otherwise causing trauma to soft tissue surfaces defining the fistula void as the adaptation (e.g., the suture) passes thereby during product deployment. Such de-epithelialization, etc. can be useful to trigger a healing response and/or otherwise facilitate the fistula healing process, for example, by enhancing certain remodeling characteristics of the implantable ECM material. In addition or alternatively, the product 20 may have a suture or other fixation device attached near an end that will become wedged in the primary opening, and the suture or other device can then be used to secure that end in place and/or to pull tissues in the region to close the primary opening over the implanted device 20. Any such suture provided can also include an attached surgical needle for use in such operations.

A suture or other similar device can be associated with the sheet form material in any suitable manner. For example, in certain aspects, a suture is glued or otherwise bonded to the material. In other aspects, a suture is coupled or linked to the material by passing one end of the suture through a small hole 25 (shown in phantom in FIG. 1) proximal the first end 22 of the material. Thereafter, this end of the suture is formed as a loop around the contained material, for example, using a knot. In still other aspects, a suture is associated with a multilaminate sheet form material by placing one end of the suture between layers prior to a bonding operation. Such bonding can be sufficient to keep the material and suture engaged, for example, as the material is drawn through the primary opening.

Figure 2:
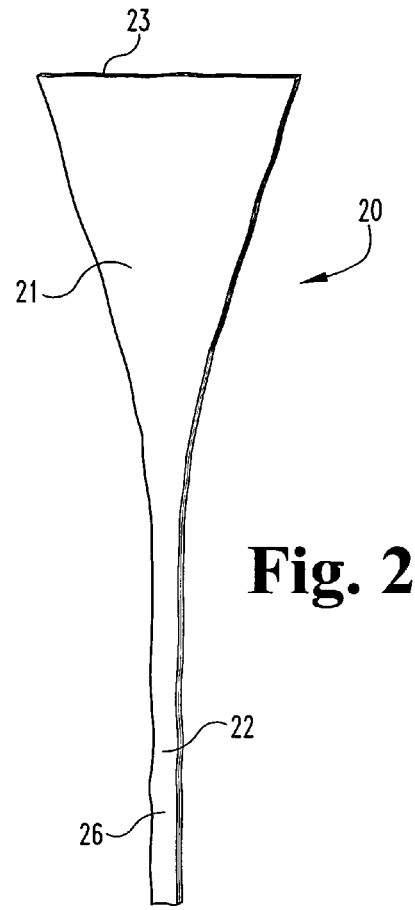
FIG. 2 is a perspective view of another medical product of the invention.

With reference now to FIG. 2, shown is a perspective view of an illustrative medical product 20 of the present invention. The product includes a compliant sheet form biocompatible material 21 similar to that of FIG. 1, except that the first end 22 includes a tail 26 or thin segment of material extending therefrom. This "tail" can be useful, for example, to pull the product 20 into a fistula tract. For example, the sheet form material 21 can be pulled into the primary opening of a fistula, tail end first, for example, by grasping the tail 26 with hemostats, etc. Thereafter, the tail 26 can be sufficiently advanced through the fistula tract so as to deform the second end 23 to conform to and fill the primary opening and/or another segment of the fistula void. The widening of the second end 23 as it moves away from the first end 22 provides increasing cross section to the formed three-dimensional volumetric body to fill at least the primary opening. The tail 26 can be long enough to exit a secondary opening. In certain aspects, the tail 26 has a total length of about 2 cm to about 10 cm, and the tapered section has a length of at least about 3 cm. In certain aspects, the tail incorporates one or more adaptations for de-epithelializing soft tissue surfaces of the fistula tract when passed therethrough.

Figure 3A:
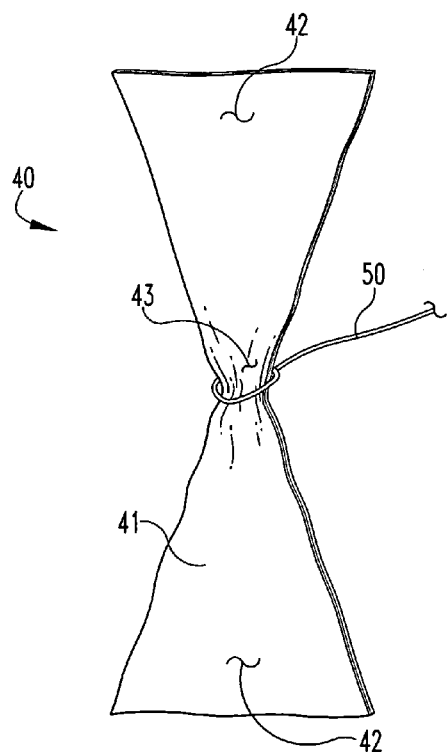
FIG. 3A is a perspective view of another medical product of the invention.
Figure 3B:
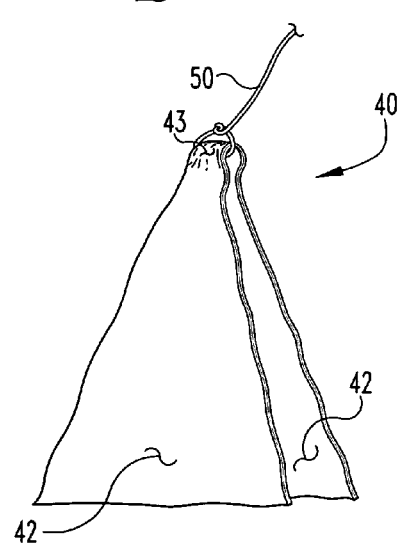
FIG. 3B is a perspective view of the medical product of FIG. 3A in a folded configuration.

FIG. 3A shows a perspective view of an illustrative medical product 40 of the present invention. The product 40 comprises a compliant sheet form biocompatible synthetic polymeric material 41 having a relatively narrow middle region 43 and two relatively wide outer regions 42 which flare out from the middle region 43. In a method for treating a fistula, the sheet form material 41 can be folded or bent at the middle region 43, for example, by associating a suture 50 with the middle region 43 and pulling as shown in FIG. 3B, or alternatively grasping and pulling the middle region 43 with tongs or another similar grasping device. Thereafter, the sheet form material 41 can be pulled into a fistula, middle region first, forcing the outer regions 42 to follow. These two outer regions 42 provide greater material surface area, for example, compared to a sheet form material including only one outer region of the same size and shape. In certain aspects, this greater material surface area can provide better occlusion of the fistula void, or any segment thereof, as the outer region materials fold and/or roll over each other upon being impinged by soft tissue surrounding, for example, the primary opening of the fistula. In certain aspects, the overall length of the sheet form material 41 is at least twice the length of the fistula being treated. In some forms, the length of the material extending from the middle region 43 to an outer regions 42 is at least about 3 cm.

Illustratively, another preferred fistula treatment method of the invention includes providing an implantable material including a compliant sheet form biocompatible material, and forcing this sheet form biocompatible material into the void so as to deform the sheet form biocompatible material into a three-dimensional volumetric body impinging upon soft tissue surfaces of the void and blocking at least a segment of the void. In certain aspects, this sheet form biocompatible material is deformable upon forcible contact against soft tissue surfaces defining the void. Such deformable materials can include any of the ECM and other biocompatible materials described herein. Further, this sheet form biocompatible material can be sized and shaped so as to be deformable to a three-dimensional volumetric body impinging upon and blocking the void at the primary opening, blocking the fistula tract (or any segment thereof), or both. In certain aspects, such a three-dimensional volumetric body, when formed, includes a portion extending into the fistula tract, and potentially protruding through a secondary opening of the fistula.

Figure 4:
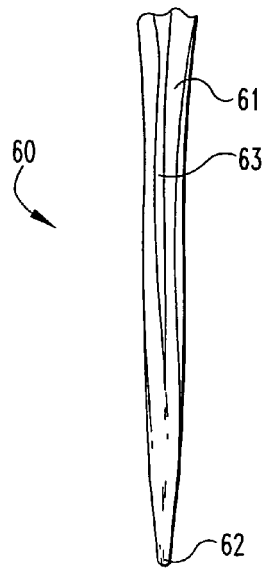
FIG. 4 is a perspective view of another medical product of the invention.
Figure 5:
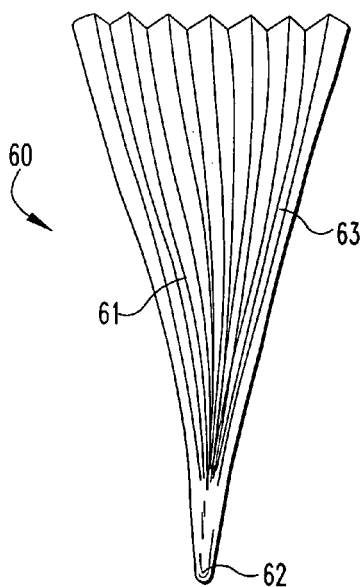
FIG. 5 is a perspective view of another medical product of the invention.

In certain embodiments, a medical product of the present invention includes an implantable material having a shaped or otherwise modified tip with at least one trailing sheet extending therefrom. Such an illustrative trailing sheet can be provided as a plurality of strands, e.g. elongate strands, such as can be formed by cutting a larger overall sheet into smaller segments that can generally run with the longitude of the device. Additionally, any number of such strands can include a plurality of cuts, such as transverse cuts, that can serve to increase the surface area of the material so as to enhance the occlusive ability of the material. For example and referring now to FIG. 4, shown is perspective view of a medical product 60 of the present invention. The product 60 comprises an implantable material 61 including a conical or conical-like tip 62 with a single sheet 63 extending therefrom. The sheet 63 may or may not be planar. In certain aspects, the sheet is convoluted, for example, including a plurality of folds or bends. In some forms, at least a portion of the sheet 63 is fan-folded, for example, as shown in FIG. 5. Further, the conical tip 62 may or may not have a continuous taper along its length, and may have portions that are rounded. The conical shape of the tip may make it easier, in certain aspects, to insert the medical product into the fistula void, tip first. In certain aspects, the tip and/or other portions of the implantable material can include barbs or other suitable adaptations for anchoring the product to soft tissue surrounding the fistula void. Such barbs and other adaptations are also useful, in some forms of the invention, to roughen up or otherwise damage (e.g., de-epithelialize) soft tissue surfaces defining the fistula void as the implantable material is passed therethrough during deployment. Such roughening up, etc. can be useful to trigger a healing response and/or otherwise facilitate the healing process.

Additionally, in certain embodiments, the tip of the strands can be formed into any suitable shape, e.g. bullet, cone, hemisphere, or cylinder, using any suitable drying technique as discussed herein. Alternatively, an illustrative device can be formed or by attaching one or more stands of sheet form material to a pre-formed tip, which can be comprised of any suitable material, remodelable, e.g. a remodelable sponge, or synthetic, e.g. absorbable or non-absorbable. The strands can be connected to the tip using any suitable connecting means, such as an adhesive, bonding, e.g. dehydrothermal, and or mechanical means, e.g. ring, fastener, or sutures. A lumen can be contained within the tip that can serve to receive a wire guide during an illustrative deployment procedure, or that can serve to provide for drainage of material through the closed fistula tract.

In other aspects, the implantable material can be made so that the center of the material is narrower than the ends, to possibly aid in inhibiting movement of the material upon deployment within the need for suturing, etc. For example, the implantable material could be configured so as to deform to a three-dimensional volumetric body wedged or lodged into the primary opening and a secondary opening. Forming a narrower center region could be accomplished in any suitable manner including but not limited to applying an ECM material band around the center of the material, tying a strip of ECM material or a resorbable suture around the center of the material, or vacuum pressing portions of the center of material.

Figure 6:
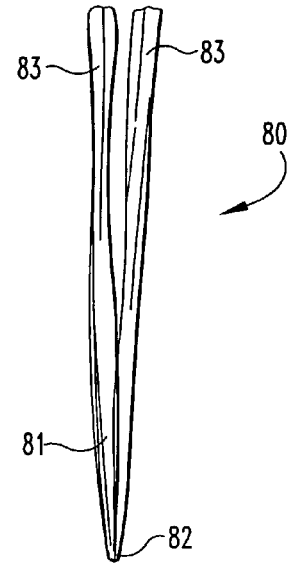
FIG. 6 is a perspective view of another medical product of the invention.
Figure 7:
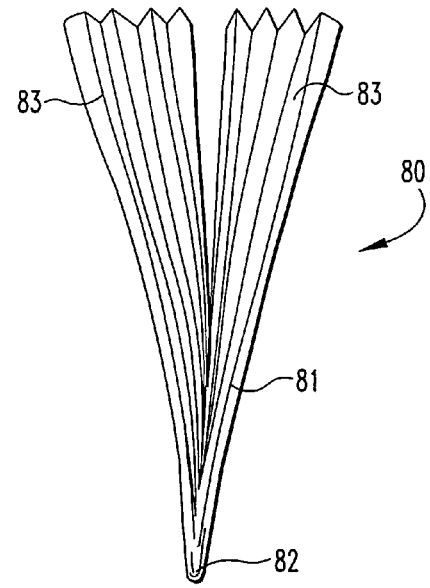
FIG. 7 is a perspective view of another medical product of the invention.

With reference now to FIG. 6, shown is a perspective view of an illustrative medical product 80 of the present invention. The product 80 comprises an implantable material 81 including a conical tip 82 with two sheets 83 extending therefrom. In certain aspects, the sheets 83 actually comprise a single piece of material folded generally in half, wherein the material fold provides the conical tip 82. In certain aspects, the material forming the conical tip 82 is further manipulated, for example, by lyophilization, vacuum pressing, or crosslinking (just to name a few) to alter one or more properties of the tip, e.g., its porosity. In other aspects, the sheets 83 comprise two pieces of material suitable joined, for example, by gluing, dehydrothermal bonding, or the like. As shown in FIG. 7, the sheets, or any portions thereof, may be fan-folded.

Figure 8:
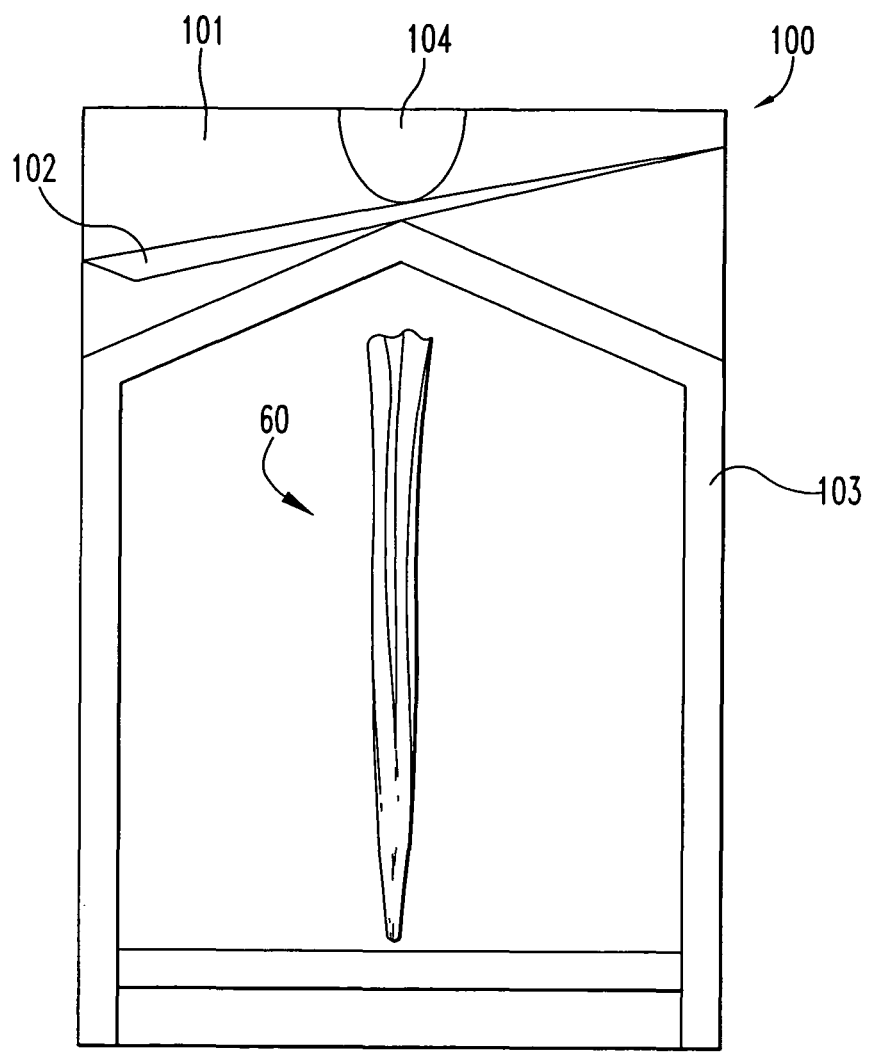
FIG. 8 provides a top view of a medical kit of the invention.

With reference now to FIG. 8, shown is a top view of an illustrative medical kit 100 of the present invention that includes medical product 60 sealed within sterile medical packaging. In particular, medical kit 100 has packaging including a backing layer 101 and a front film layer 102 (shown partially drawn away from backing layer 101). The medical product is sealed between backing layer 101 and film 102 utilizing a boundary of pressure-adhesive 103 as is conventional in medical packaging. A cut-out 104 may be provided in the backing layer 101 to assist a user in separating the film layer 102 from the backing layer 101.

Sterilization of the medical kit 100 may be achieved, for example, by irradiation, ethylene oxide gas, or any other suitable sterilization technique, and the materials and other properties of the medical packaging will be selected accordingly. Also, medical products of the invention can be contained in sterile packaging in any suitable state. Suitable states include, for example, a hydrated or dehydrated state. The medical products can be dehydrated by any means known in the art (e.g., lyophilization or air dried). If a medical products of the present invention is stored in a dehydrated state, it is preferred that it retains all of its biological and mechanical properties (e.g., shape, density, flexibility, etc.) upon rehydration.

The materials and other properties of the packaging will be selected accordingly. For example, the package can include indicia to communicate the contents of the package to a person and/or a machine, computer, or other electronic device. Such indicia may include the dimensions of, the type of materials used to form, and/or the physical state of, the contents of the package. In certain embodiments, a medical product is packaged for sale with instructions for use. For example, in a particularly preferred embodiment, a medical kit includes at least one medical product sealed within a sterile package, wherein the packaging has visible indicia identifying the at least one medical product as having physical characteristics as disclosed herein, and/or can contain or otherwise be associated with printed materials identifying the contents as having such physical characteristics and including information concerning its use as a medical product for treating fistulae. The packaging can also include visible indicia relating to the dimension of the at least medical product, and/or relating to the treatment site(s) for which the at least one medical product is configured.

The present invention also provides a line of medical kits, wherein a medical kit of the invention includes one or more medical products such as those disclosed herein enclosed within a sealed package. When the medical kit includes more than one medical product, for example, a plurality of medical products, the products can each be of substantially the same size and shape, or, alternatively, can vary with respect to size and shape.

The medical products of the invention can be modified before, during, and/or after deployment. Illustratively, a product may be cut, trimmed, sterilized, and/or treated (e.g., brought into contact, impregnated, coated, etc.) with one or more desirable compositions, such as any of those previously disclosed herein, e.g., anticoagulants (e.g., heparin), growth factors or other desirable property modifiers. In certain aspects, following deployment of a sheet form biocompatible material in accordance with the present invention, one or more portions of the material are trimmed off or otherwise removed, for example, material protruding from the primary opening and/or any secondary opening.

Further, any exogenous bioactive substances incorporated into ECM material of the invention may be from the same species of animal from which the ECM material was derived (e.g. autologous or allogenic relative to the ECM material) or may be from a different species from the ECM material source (xenogenic relative to the ECM material). In certain embodiments, the ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

In certain aspects, medical products of the invention incorporate an adhesive or, where appropriate, a sclerosing agent to facilitate and/or promote blocking of the fistula void. As well, fistula treatment methods of the invention can include steps where such substances or materials are applied to a medical product being deployed and/or to the soft tissues surrounding the fistula. For example, an adhesive, glue or other bonding agent may also be used in achieving a bond between a medical product of the invention and the soft tissues surrounding the fistula void. Suitable bonding agents may include, for example, fibrin or collagen gels or pastes, gelatin, or other agents including reactive monomers or polymers, e.g., cyanoacrylate adhesives. In some forms of the invention, a fistula treatment method includes contacting soft tissue surfaces surrounding the fistula, e.g., soft tissue surfaces at or near the primary opening and/or soft tissues lining the fistula tract, with a sclerosing agent prior to forcing the sheet from material into the fistula. Such use of a sclerosing agent can de-epithelialize or otherwise damage or disrupt these soft tissue surfaces, leading to the initiation of a healing response.

In certain aspects, fistula treatment methods of the invention include an endoscopic visualization (fistuloscopy) step. Such endoscopic visualization can be used, for example, to determine the shape and size of the fistula, which in turn can be used to select an appropriately sized and shaped medical product for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, cleaning of the fistula can be performed prior to and/or during deployment of a medical product of the invention. For example, an irrigating fluid can be used to remove any inflammatory or necrotic tissue located within the fistula prior to engrafting the product. In certain embodiments, one or more antibiotics are applied to the medical product and/or the soft tissues surrounding the fistula as an extra precaution or means of treating any residual infection within the fistula.

In other embodiments, a fistula is drained prior to receiving a medical product of the invention therein. Such draining can be accomplished by inserting a narrow diameter rubber drain known as a seton (Greek, "thread") through the fistula. The seton is passed through the fistula tract and tied as a loop around the contained tissue and left for several weeks or months, prior to definitive closure or sealing of the fistula. This procedure is usually performed to drain infection from the area, and to mature the fistula tract prior to a definitive closure procedure.

Further, the fistula treatment methods described herein can be used to close one or more fistula during a given medical procedure. Also, the methods of the invention can be used to treat complex fistula. For multiple fistula, multiple medical products can be engrafted until all the fistula have been addressed. In cases of complex fistula, for example a horse-shoe fistula, there may be one primary opening and two or more fistula tracts extending from that opening. In such instances, a medical product may be configured with one head component and two or more tail components. Each "tail" can be drawn into the primary opening, and thereafter into one of the fistula tracts extending therefrom. Sufficient pulling force can be applied to wedge the head component snugly into the primary opening. Each of the tails and/or the head of the product can be secured by sutures and/or an adhesive, if necessary, and any excess material can be trimmed.

Also, the invention provides, in certain aspects, methods for treating fistulae that include providing a sheet form biocompatible material that is sized and shaped so as to be deformable to a three-dimensional volumetric body impinging and/or being impinged by soft tissues surrounding the fistula so as to block the void at the primary opening, block the fistula tract (or any segment thereof), or both. In some aspects, the invention provides methods for blocking an opening anywhere on or within the body of a patient, for example, blocking the primary opening (or any other segment) of a urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method of treating a fistula having at least a primary opening, a secondary opening and a fistula tract extending therebetween, the method comprising:
    providing a medical graft device that includes a deformable sheet form biocompatible material comprising a plurality of separate elongate sheet form trailing members each having a width between a first lateral edge and a second lateral edge, a first face extending between the first lateral edge and the second lateral edge, and a second face opposing the first face, and a sheet thickness between the first face and the second face, wherein the first and second lateral edges diverge toward a distal end defining a distalmost edge of the sheet form trailing member such that the width of the sheet form trailing member is wider near the distal end than at a leading end, wherein the distalmost edge of each sheet form trailing member is unadjoined to the distalmost edges of each other sheet form trailing member, said plurality of separate elongate trailing members is configured to be deformable upon implantation to a three dimensional volumetric body, said three dimensional volumetric body having an outer surface formed from portions of said sheet form trailing members which contact and impinge upon surrounding tissues;
    providing a pulling device suitable to traverse the fistula tract;
    passing the pulling device through the fistula tract from the secondary opening and toward the primary opening so as to position an end of the pulling device proximate the primary opening;
    securing the pulling device to the leading end of the medical graft device; and
    pulling the leading end of the medical graft device through the fistula tract toward the secondary opening with the pulling device so that the medical graft device extends from the first opening through the fistula tract and said deformable sheet form biocompatible material includes a portion protruding from the second opening, so as to deform the plurality of separate elongate sheet form trailing members within the primary opening to conform to and to block and fill the primary opening with the sheet form biocompatible material.

2. The method of claim 1, wherein said biocompatible material comprises a remodelable material.

3. The method of claim 2, wherein said remodelable material comprises a remodelable extracellular matrix material.

4. The method of claim 3, wherein said remodelable extracellular matrix material comprises submucosa.

5. The method of claim 1, wherein said medical graft device includes a conical tip from which the plurality of separate elongate trailing members extend, said plurality of separate elongate trailing members comprising at least one segment of said sheet form biocompatible material.

6. The method of claim 5, wherein said at least one segment of sheet material is convoluted.

7. The method of claim 6, wherein said at least one segment of sheet material includes a plurality of folds.

8. The method of claim 7, wherein said at least one segment of sheet material is fan-folded.

9. The method of claim 1, wherein said medical graft device includes a conical tip from which the plurality of separate elongate trailing members extend, said plurality of separate elongate trailing members comprising at least two segments of said sheet form biocompatible material.

10. The method of claim 1, wherein said deformed sheet form biocompatible material includes a portion extending into the fistula tract.

11. A method of treating a fistula having a primary opening in the alimentary canal, the fistula defining a void through soft tissues, the void including a fistula tract extending between a primary opening and a secondary opening, the method comprising:
    providing a medical graft device that includes a deformable sheet form biocompatible material comprising a plurality of separate elongate sheet form trailing members each having a width between a first lateral edge and a second lateral edge, and a first face extending between the first lateral edge and the second lateral edge, and wherein the width of the trailing member is wider toward a flared distal end defining a distalmost edge of the sheet form trailing member than at a leading end, wherein the distalmost edge of each sheet form trailing member is unadjoined to the distalmost edges of each other sheet form trailing member, said plurality of separate elongate trailing members configured to be deformable upon implantation to a three dimensional volumetric body, said three dimensional volumetric body having an outer surface formed from portions of said sheet form trailing members which contact and impinge upon surrounding tissues;
    pulling a leading end of the sheet form biocompatible material into the fistula void through the primary opening and through the fistula void to the secondary opening so that the biocompatible material extends from the first opening through the fistula void and out of the secondary opening, said pulling causing the plurality of separate elongate sheet form trailing members to deform upon forcible contact against soft tissue surfaces, into a three-dimensional volumetric body impinging upon soft tissue surfaces of the void and blocking and filling the void with the sheet form biocompatible material.

12. The method of claim 11, wherein said leading end is pulled into the fistula void through the primary opening.

13. The method of claim 11, wherein said leading end is pulled through the fistula void with a pulling device connected to said leading end.

14. A method of treating a fistula void extending through tissue of a patient, the fistula void having a first opening occurring in the alimentary canal, a second opening, and a fistula tract extending therebetween, the method comprising:
providing a medical graft device having a sufficient length to span the fistula tract and including a deformable sheet form biocompatible material comprising a plurality of separate elongate sheet form trailing members each having a first lateral edge and a second lateral edge the first and second lateral edges, and a first face extending between the first lateral edge and the second lateral edge, and wherein the width of the trailing member is wider toward a flared distal end defining a distalmost edge of the sheet form trailing member than at a leading end, wherein the distalmost edge of each sheet form trailing member is unadjoined to the distalmost edges of each other sheet form trailing member, said plurality of separate elongate trailing members configured to be deformable upon implantation to a three dimensional volumetric body, said three dimensional volumetric body having an outer surface formed from portions of said sheet form trailing members which contact and impinge upon surrounding tissues; and
forcing a leading end of the medical graft device into the fistula void through said first opening and through the fistula void to the second opening so that the medical graft device extends from the first opening through the fistula tract and out of the second opening, said forcing causing said plurality of separate elongate sheet form trailing members to deform, upon forcible contact against soft tissue surfaces, to a three dimensional volumetric body filling at least the first opening of the fistula void with the sheet form biocompatible material; wherein said three dimensional volumetric body substantially fills the fistula tract and is occupied by gathered portions of the sheet form material.

15. The method of claim 14, wherein said sheet form biocompatible material includes at least one tapered portion.

16. A method of plugging a fistula having a fistula tract occurring in a wall of patient tissue having a primary opening and a secondary opening, the method comprising:
providing a deformable sheet form biocompatible material comprising a plurality of separate elongate sheet form trailing members each having a width between a first lateral edge and, a second lateral edge, and a first face extending between the first lateral edge and the second lateral edge, and wherein the width of the trailing member is wider toward a flared distal end defining a distalmost edge of the sheet form trailing member than at a leading end; and
pulling said sheet form material at a leading end thereof so as to advance the sheet form material into the fistula tract through the primary opening in a first direction through the fistula tract to the second opening so that the biocompatible material extends from the first opening through the fistula tract and out of the secondary opening, wherein said sheet form material is sized and shaped such that as said sheet form material moves through the fistula opening in said first direction tissue surrounding the fistula tract is effective to force said sheet form material into a progressively more compacted condition so as to wedge the sheet form material into the fistula tract and to plug and fill the fistula tract with the sheet form biocompatible material, wherein the sheet form material wedged into the fistula opening includes said elongate sheet form trailing members in a rolled and/or folded condition contacting surrounding patient tissue, said rolled and/or folded condition created during said pulling.

17. A method for treating a fistula defining a void through soft tissues, the void including a fistula tract extending between a primary opening in the alimentary canal and a secondary opening, the method comprising:
providing an implantable device that includes a deformable sheet form biocompatible material, said implantable device including a leading portion and a trailing portion, and wherein said trailing portion comprises a plurality of elongate sheets each sheet comprising a portion of the biocompatible material having a first face opposing a second face, a leading end and a trailing end and diverging lateral edges extending therebetween, the trailing end being wider than the leading end, wherein said sheet form biocompatible material includes a plurality of folds or bends, and wherein said sheet form biocompatible material comprises at least two layers of material each having at least one free edge; and
forcing the sheet form biocompatible material into the fistula void through the primary opening and through the fistula tract and to the secondary opening so that the sheet form biocompatible material extends from the first opening through the fistula tract and out of the secondary opening, said forcing causing the sheet form biocompatible material to deform into a three-dimensional volumetric body contacting and impinging upon soft tissue surfaces of the fistula void and blocking and filling the fistula void including the primary opening with the sheet form biocompatible material, wherein said forcing includes pulling at a leading end of the sheet form material so as to advance the leading end through the fistula tract away from the primary opening.

18. The method of claim 17, wherein said at least two layers of material are bonded to one another.

19. The method of claim 17, wherein said deformable sheet form biocompatible material comprises a synthetic polymeric material.

20. The method of claim 19, wherein said synthetic polymeric material is poly(glycolic acid-co-trimethylene carbonate).

21. The method of claim 17, wherein said deformable sheet form biocompatible material comprises an extracellular matrix material.

22. The method of claim 21, wherein said extracellular matrix material comprises serosa, pericardium, submucosa, dura mater, peritoneum, or dermal collagen.

23. The method of claim 17, wherein said deformable sheet form biocompatible material is effective to promote tissue ingrowth from the soft tissues.

24. The method of claim 17, wherein said deformable sheet form biocompatible material is non-planar.

25. The method of claim 17, wherein said trailing portion comprises a piece of material folded generally in half to form two sheet form trailing portions.

26. The method of claim 17, wherein said forcing causes the trailing end to become wedged into the primary opening.

27. The method of claim 17, wherein the fistula is an anorectal fistula.

* * * * *